United States Patent
Masuda et al.

(10) Patent No.: US 7,700,647 B2
(45) Date of Patent: Apr. 20, 2010

(54) FLUORINATED BIS (PHTHALIC ANHYDRIDE) AND METHOD FOR PRODUCING THE SAME

(75) Inventors: Go Masuda, Suita (JP); Yasunori Okumura, Kobe (JP); Shinji Nishimae, Kyoto (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/007,101

(22) Filed: Jan. 7, 2008

(65) Prior Publication Data

US 2008/0119659 A1  May 22, 2008

Related U.S. Application Data

(62) Division of application No. 10/868,874, filed on Jun. 17, 2004, now abandoned.

(30) Foreign Application Priority Data

Jun. 17, 2003  (JP) .................. 2003-172046
Jul. 24, 2003  (JP) .................. 2003-201123

(51) Int. Cl.
    *A61K 31/343* (2006.01)
(52) U.S. Cl. ................................... 514/470
(58) Field of Classification Search ............ 514/470
    See application file for complete search history.

(56) References Cited

U.S. PATENT DOCUMENTS

| | | | |
|---|---|---|---|
| 2,411,567 A | 11/1946 | Fisher | |
| 3,956,320 A | 5/1976 | Heath et al. | |
| 4,659,842 A | 4/1987 | Vahlenkamp et al. | |
| 4,870,194 A | 9/1989 | Molinaro et al. | |
| 5,021,168 A | 6/1991 | Molinaro et al. | |
| 5,336,788 A | 8/1994 | Lesins | |
| 6,048,986 A * | 4/2000 | Ando et al. | 549/239 |

FOREIGN PATENT DOCUMENTS

| | | |
|---|---|---|
| EP | 0 438 382 | 7/1991 |
| EP | 0 480 266 | 4/1992 |
| JP | 51-23498 | 7/1976 |
| JP | 54-63039 | 5/1979 |
| JP | 62-42980 | 2/1987 |
| JP | 62-116572 | 5/1987 |
| JP | 1-254673 | 10/1989 |
| JP | 2-306945 | 12/1990 |
| JP | 3-101673 | 4/1991 |
| JP | 3-176484 | 7/1991 |
| JP | 4-334346 | 11/1992 |
| JP | 5-1148 | 1/1993 |
| JP | 6-1914 | 1/1994 |
| JP | 6-16615 | 1/1994 |
| JP | 7-206845 | 8/1995 |
| JP | 7-278544 | 10/1995 |
| JP | 8-333322 | 12/1996 |
| JP | 9-31014 | 2/1997 |
| JP | 9-505287 | 5/1997 |
| JP | 10-30013 | 2/1998 |
| JP | 3130653 | 11/2000 |
| JP | 2001-335571 | 12/2001 |
| JP | 2002-332253 | 11/2002 |
| JP | 2002-332268 | 11/2002 |
| JP | 2003-238515 | 8/2003 |
| WO | 95/14000 | 5/1995 |

OTHER PUBLICATIONS

International Search Report mailed Aug. 3, 2004 in PCT Application No. PCT/JP2004/008829.

Notification of Reasons for Refusal issued May 20, 2008 in Japanese Application No. 2003-201123 (one of the base applications of the present application), and the English translation thereof.

Ando, S. et al. *Perfluorinated Polyimide Synthesis*, Macromolecules, vol. 25, (1992), pp. 5858-5860.

(Continued)

*Primary Examiner*—Rebecca L Anderson
*Assistant Examiner*—Shawquia Young
(74) *Attorney, Agent, or Firm*—Wenderoth, Lind & Ponack, L.L.P.

(57) ABSTRACT

It is an object of the present invention to provide fluorinated bis(phthalic anhydride) which has less coloration and higher solubility in comparison with conventional compounds, and a method for producing the same. Further, it is also an object of the present invention to provide a method for producing a fluorinated bis(phthalonitrile) compound, which is an intermediate raw material compound of the method for producing the fluorinated bis(phthalic anhydride), and a polyamic acid and a polyimide, which are produced from the fluorinated bis(phthalic anhydride). A fluorinated bis(phthalic anhydride) of the present invention is the fluorinated bis(phthalic anhydride) represented by the following formula ($I^1$), wherein its specific surface area is 3.0 m²/g or larger. It is also characterized in that its molar absorption coefficient is 0.6 L/mol·cm or less at a wavelength of 360 nm.

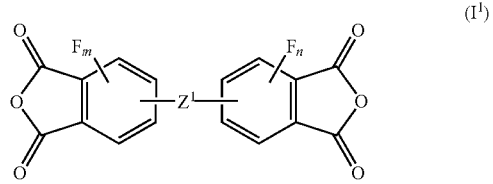

($I^1$)

[wherein, m and n independently represent integers of 1 to 3, and $Z^1$ represents a single bond group or a bivalent organic group.]

4 Claims, No Drawings

OTHER PUBLICATIONS

Solvent Handbook, 6$^{th}$ ed. Kodansha Ltd., 1985. pp. 47-51, with Partial English Translation.

Keller, M. et al. *The Synthesis of Highly Fluorinated Phthalonitrile Resins and Cure Studies*, J. of Fluorine Chemistry, vol. 13, (1979), pp. 315-324.

Supplementary European Search Report issued in Application No. 04746298.1, dated Sep. 8, 2008.

Falbe et al., "ROMPP Lexikon Chemie, 10.Auflage, Band 3: H-L", 1997, G. Thieme Verlag, Stuttgart, XP002493445.

Notification of Reasons for Refusal dispatched Jun. 30, 2009, in corresponding Japanese Application No. 2004-179912, and English translation thereof.

Decision of Rejection issued Jan. 19, 2010 in corresponding Japanese Application No. 2004-179912.

* cited by examiner

FLUORINATED BIS (PHTHALIC ANHYDRIDE) AND METHOD FOR PRODUCING THE SAME

This application is a divisional of U.S. application Ser. No. 10/868,874, filed Jun. 17, 2004 now abandoned.

This application claims benefit of priority to Japanese patent application No. 2003-172046, filed on Jun. 17, 2003 and No. 2003-201123, filed on Jul. 24, 2003, the contents of which are incorporated by reference herein.

BACKGROUND OF THE INVENTION

1. Field of the Invention

The present invention relates to fluorinated bis(phthalic anhydride) which is useful as intermediate raw materials of optical materials and the like, and a method for producing the same.

2. Description of the Related Art

Polyimide, which is highly fluorine-substituted, is useful as optical materials, wiring board materials, photosensitive materials, liquid crystal materials, or the like. This polyimide is produced by hydrolyzing a fluorine-substituted bis(phthalonitrile) compound to form a bis(phthalic acid) compound, dehydrating the bis(phthalic acid) compound to form bis(phthalic anhydride), then condensing the bis(phthalic anhydride) and a diamine compound to form polyamic acid, and further dehydrating the polyamic acid. However, various problems are caused when this production process are performed particularly in industrial mass synthesis.

For example, as the bis(phthalonitrile) compound which is a synthetic intermediate of polyimide, there is known 1,4-bis(3,4-dicyano-2,5,6-trifluorophenoxy)tetrafluorobenzene (hereinafter, referred to as "10 FEDN"). By this compound, excellent polyimide can be produced. This compound is generally obtained by following a synthetic route shown below and using 3,4,5,6-tetrafluorophthalonitrile (hereinafter, referred to as "TFPN") and tetrafluorohydroquinone (hereinafter, referred to as "TFHQ") as raw materials

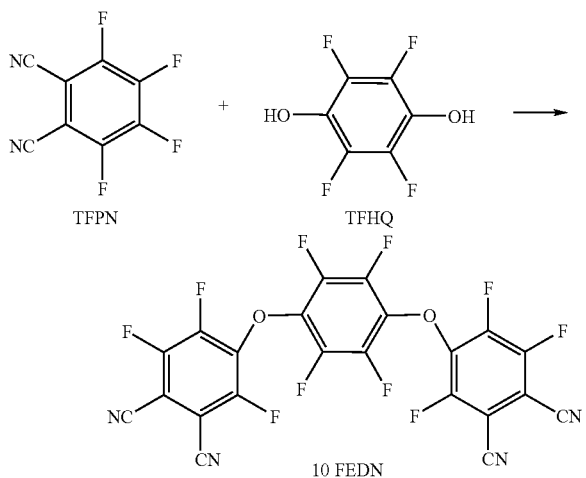

In accordance with the above-mentioned synthetic route, it is thought that in theory, 2 equivalent amount of TFPN may be reacted with respect to TFHQ. However, under such a condition, a side reaction shown below occurs. That is, there was a problem that, as shown below, the compound formed by condensing TFPN and TFHQ in proportions of 1:1 reacted not with the TFPN but with 10FEDN, which is an intended compound, and the yield and the purity of the intended compound (10FEDN) extremely deteriorated.

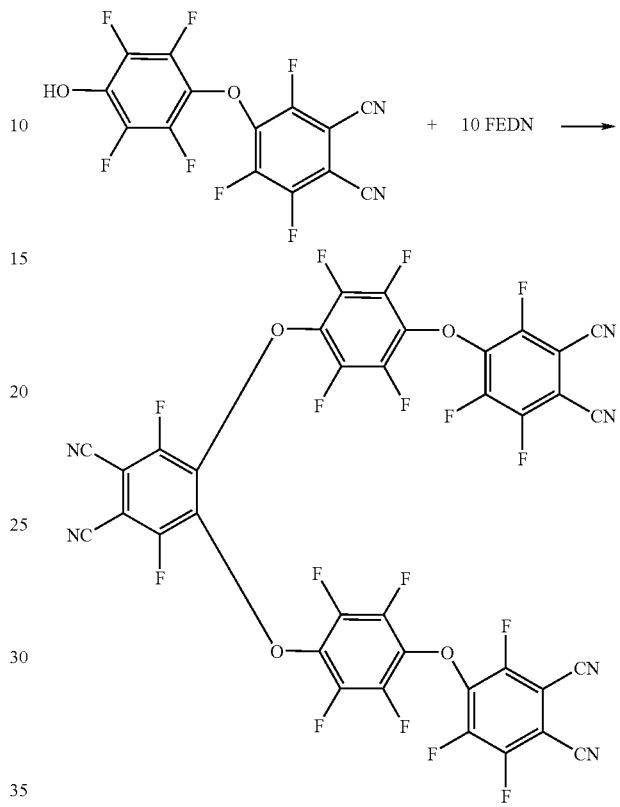

Technology described in Japanese Unexamined Patent Publications No. 6-16615 succeeded in attaining a fluorinated bis(phthalonitrile) compound having a high purity by using TFPN in an amount of 8 molar equivalent or more with respect to TFHQ. A method for producing a fluorinated bis (phthalonitrile) compound described in Japanese Unexamined Patent Publications No. 8-333322 is a method in which TFPN is also used in excess, and it facilitates purification by using a solvent which is hardly soluble in water.

In the purification processes employed in these conventional art, the intended compounds are purified with column chromatography after removing the raw material compound such as TFPN, which has not yet reacted and remains in excess in a reaction solution, by distillation. However, 10FEDN, which is an intended compound, is easily affected by heat, and therefore an operation temperature cannot be increased so much in a purification process. On the other hand, since TFPN, which is a raw material compound, has a melting point of 87° C. and is solid at room temperature, a reduced-pressure condition is required for removing by distillation. Therefore, when a fluorinated phthalonitrile derivative was produced by the conventional technology, it was necessary to perform the distillation under reduced-pressure in the purification process and this method was not suitable for mass synthesis at a plant level. Furthermore, there was a problem that since a distillation temperature could not be raised in the distillation under reduced-pressure in this purification process as described above, 10FEDN and others was solidified as the raw material compound was distilled off.

Thus, a method which avoids a distillation process has been desired in the purification process in the production of the fluorinated bis(phthalonitrile) compound. However, column chromatography and the like, which is a purification technique other than distillation, have the problems of an equipment cost and the like. Accordingly, as a purification process for the mass synthesis of the fluorinated bis(phthalonitrile) compound, a purification by recrystallization is ideal.

However, according to the rule of common sense in the synthetic organic chemical field, a compound having less impurities (particularly impurities having a structure similar to these compound) is apt to crystallization. Conversely, when a raw material compound having a structure in common with the intended compound is present as an impurity in a large amount in a reaction system, purification by recrystallization of the intended compound is difficult. Therefore, in the production of the fluorinated bis(phthalonitrile) compound, where the raw material compound is remaining excessively in a reaction system after the completion of a reaction, it was considered to be difficult that a recrystallization process is applied to the purification process.

Also, a process, in which a bis(phthalic anhydride) is produced by dehydrating a bis(phthalic acid) compound, has also a problem. It is thought that as such the dehydration reaction, a known method is applied. As an examples of such the known method, there is described a method, in which only acetic anhydride is added to a mixture of 2,3,3',4'-biphenyl-tetracarboxylic acid and 3,4,3',4'-biphenyltetracarboxylic acid and this mixture is heated to obtain biphenyltetracarboxylic anhydride, in a example in Japanese Unexamined Patent Publications No. 51-23498. Similarly, in the technology described in Japanese Unexamined Patent Publications No. 62-116572, 3,4,3',4'-biphenyltetracarboxylic anhydride is produced using acetic anhydride as a solvent, and the concentration of 3,4,3',4'-biphenyltetracarboxylic acid, which is a raw material compound, is specified for the purpose of improving handling through an increase in a crystal size and reducing coloration contents.

However, if the methods of these patent references are applied to the production of the fluorinated bis(phthalic anhydride) as it is, not only yield may deteriorates due to the occurrence of a side reaction but also the intended compound may colored. It is conceivable as one of causes that since a fluorinated bis(phthalic acid) compound, which is a raw material compound, exhibits extremely high solubility in acetic anhydride or acetic acid, a reaction proceeds excessively and a dehydration reaction occurs between the raw material compounds instead of the dehydration between adjacent carboxyl groups in a molecule. On the other hand, when the concentration of raw material compounds in acetic anhydride are decreased in order to suppress such the side reaction as with the technology described in Japanese Unexamined Patent Publications No. 62-116572, purification of the intended compound is difficult and the loss of the intended compound becomes greater. Furthermore, this technology requires contacting with an organic solvent prior to the dehydration reaction in order to enhance an effect.

A method for producing fluorinated phthalic anhydride by dehydrating phthalic acid, which is highly fluorine-substituted, is described, for example, in Japanese Unexamined Patent Publications No. 2-306945. That is, there is disclosed in this reference a method of obtaining tetrafluorophthalic anhydride by heating tetrafluorophthalic acid in the presence of an organic solvent such as xylene or toluene. However, in case where this method is applied to the production of the fluorinated bis(phthalic anhydride), since the fluorinated bis(phthalic acid) compound, which is a raw material compound, has relatively low solubility in xylene and the like, a reaction must be a slurry reaction and therefore it may take too much time to react or the intended compound having a high purity may not attained by using only xylene and the like. Therefore, this method cannot be adopted as a method of mass synthesis of the fluorinated bis(phthalic anhydride).

On the other hand, in Japanese Patent Publications No. 3130653, there is disclosed a method of synthesizing the fluorinated bis(phthalic anhydride). In this method, dehydration is performed by heating the fluorinated bis(phthalic acid) compound in a solvent such as thionyl chloride, and this method accomplishes certain results. However, since this reaction is carried out in a slurry condition, optimal reaction conditions varies due to a small difference in conditions, for example, a reaction time varies significantly with reaction scales or material lots. Further, since a extremely reactive dehydrating agent such as thionyl chloride is used, the intended compound is readily colored and it is difficult to attain products of high quality. Furthermore, there is also a problem that the fluorinated bis(phthalic anhydride) obtained by this method has a small specific surface area and is not insufficient in solubility.

As described above, there are known methods of synthesizing the fluorinated bis(phthalonitrile) compound and the fluorinated bis(phthalic anhydride), which is a synthetic intermediate of highly fluorine-substituted polyimide, and methods considered to be applicable to its synthesis.

However, in the conventional methods, efficiency was low and it was difficult to expand the scale of implementation to a plant level of mass synthesis. Additionally, since the fluorinated bis(phthalic anhydride) attained by the conventional methods has a small specific surface area and low solubility, an efficiency at the next step may deteriorates. Further, it becomes important to reduce further a coloration of a synthetic intermediate, since particularly when polyimide, final products, is used as optical materials, the coloration becomes a problem.

BRIEF SUMMARY OF THE INVENTION

It is an object to be solved by the present invention to provide fluorinated bis(phthalic anhydride) which has less coloration and higher solubility in comparison with conventional compounds, and a method for producing the same. Further, it is also an object of the present invention to provide a method for producing a fluorinated bis(phthalonitrile) compound and bis(phthalic anhydride), which are raw material compounds of the method for producing the fluorinated bis (phthalic anhydride), as well as a polyamic acid and polyimide, which are produced from the fluorinated bis(phthalic anhydride).

As a result of studying intensely in order to resolve the above problems, the present inventors have found that it is possible to attain efficiently fluorinated bis(phthalic anhydride) having excellent characteristics as a synthetic intermediate of polyimide by dehydrating using a specific acid anhydride in the presence of an appropriate organic solvent and completed the present invention.

A fluorinated bis(phthalic anhydride) of the present invention is the fluorinated bis(phthalic anhydride) represented by the following formula ($I^1$), wherein its specific surface area is 3.0 m$^2$/g or larger. It is also characterized in that its molar absorption coefficient is 0.6 L/mol·cm or less at a wavelength of 360 nm.

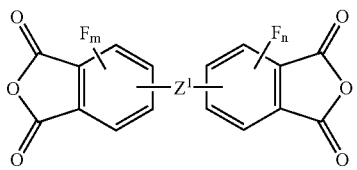

(I¹)

[wherein, m and n independently represent integers of 1 to 3, and $Z^1$ represents a single bond group or a bivalent organic group.]

A method for producing the fluorinated bis(phthalic anhydride) (I¹) according to the present invention is a method in which a fluorinated bis(phthalic acid) compound (II¹) is used as a raw material, and fluorinated bis(phthalic acid) compound (II¹) is dehydrated by using an aliphatic carboxylic anhydride in an organic solvent.

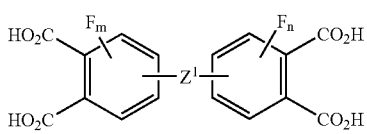

(II¹)

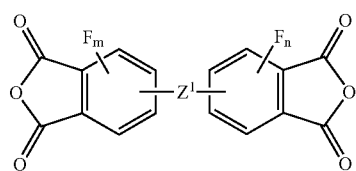

(I¹)

[wherein, m, n and $Z^1$ represent the same one as described above.]

As the above-mentioned organic solvent, an aromatic hydrocarbon and/or an aliphatic hydrocarbon are/is preferably used. The reason for this is that use of these hydrocarbons moderately suppress the excessive proceeding of the reaction due to use of an aliphatic carboxylic anhydride, and enables a reaction having high reproducibility. In treatment after the completion of the reaction, it is preferred that an intended compound is crystallized by adding a poor solvent. The reason for this is that in aftertreatment in which water is used, a reverse reaction that a dicarboxylic acid is produced from an anhydride may occur, and when an intended compound is crystallized by this method after the above reaction, a fluorinated bis(phthalic anhydride), which has a large specific surface area and exhibits excellent solubility, can be attained.

A method for producing a fluorinated bis(phthalonitrile) compound (V), which is a raw material compound of a compound, in which a $Z^1$ group is a bivalent organic group, among the above-mentioned fluorinated bis(phthalic acid) compound (II¹) is a method, wherein a fluorinated phthalonitrile derivative (III) and a compound (IV) are condensed as shown in the following formula:

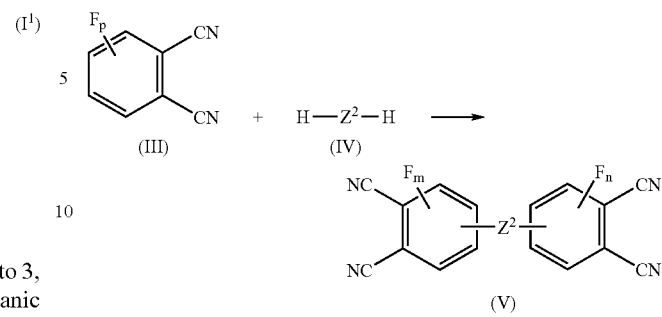

[wherein, p represents an integer of 2 to 4, $Z^2$ represents a bivalent organic group, and m and n independently represent integers of 1 to 3.]; the fluorinated phthalonitrile derivative (III) was used in excess over the compound (IV); and after the condensation, the fluorinated bis(phthalonitrile) compound (V) is separated from the remaining fluorinated phthalonitrile derivative (III) through the use of the difference between solubility thereof in an organic solvent.

In addition, a method for producing a fluorinated bis(phthalic anhydride) (I²), in which a $Z^1$ group is a bivalent organic group, among the fluorinated bis(phthalic anhydride) (I¹) is a method, wherein a fluorinated phthalonitrile derivative (III) and a compound (IV) are condensed to form the fluorinated bis(phthalonitrile) compound (V), this compound (V) is hydrolyzed to obtain a fluorinated bis(phthalic acid) (II²), and this acid (II²) is dehydrated to produce the fluorinated bis(phthalic anhydride) (I²) as shown in the following formula:

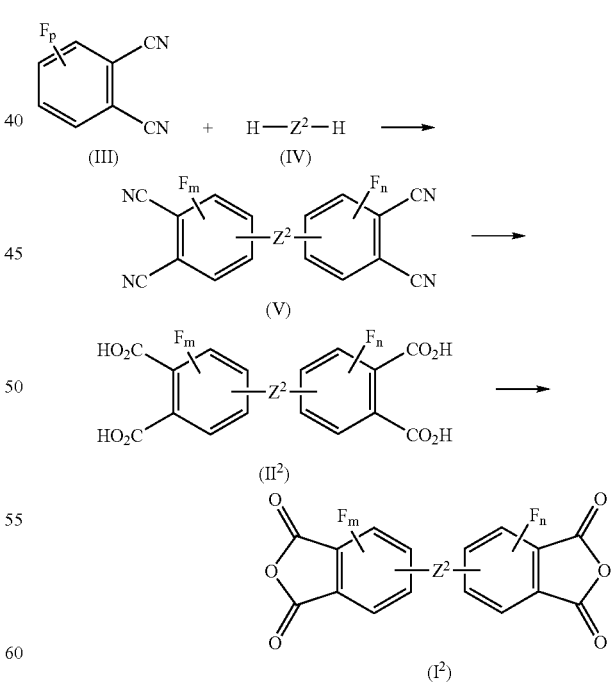

[wherein, p, Z, m and n represent the same one as described above.]; the fluorinated phthalonitrile derivative (III) was used in excess over the compound (IV); after the condensation, the fluorinated bis(phthalonitrile) compound (V) is separated from the remaining fluorinated phthatonitrile derivative (III) through the use of the difference between solubility thereof in an organic solvent; and the fluorinated bis(phthalic acid) compound (II²) is dehydrated using an aliphatic carboxylic anhydride in an organic solvent.

Further, a polyamic acid of the present invention represented by the following formula (VII) is produced by using the above-mentioned fluorinated bis(phthalic anhydride) and a diamine compound (VI) as raw materials.

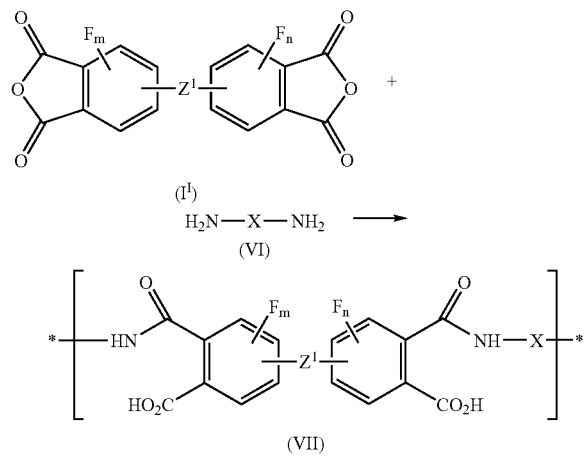

[wherein, m, n, $Z^1$ and X represent the same one as described above.]

Additionally, polyimide of the present invention represented by the following formula (VIII) is produced by using the above-mentioned polyamic acid (VII) as a raw material.

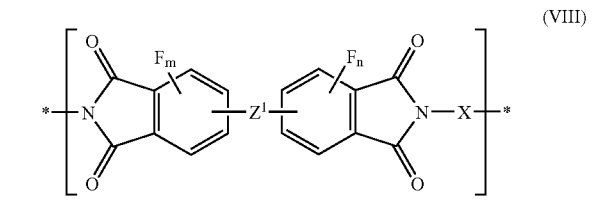

[wherein, m, n, $Z^1$ and X represent the same one as described above.]

DETAILED DESCRIPTION OF THE INVENTION

Hereinafter, the embodiments of the present invention and the effects thereof will be described.

A fluorinated bis(phthalic anhydride) of the present invention can be produced by the following scheme using a fluorinated bis(phthalic acid) compound (II¹) as a raw material.

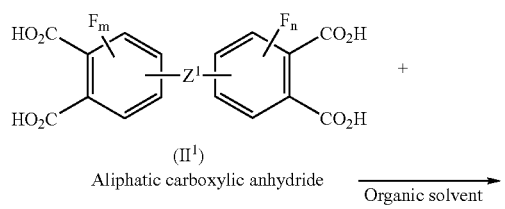

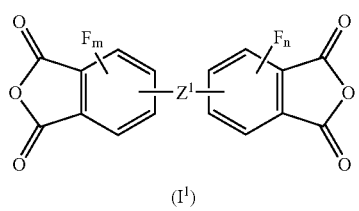

[wherein, m, n and $Z^1$ represent the same one as described above.]

The above-mentioned scheme shows a process of dehydrating a fluorinated bis(phthalic acid) compound (II¹) and capturing produced water molecule with an aliphatic carboxylic anhydride to synthesize a fluorinated bis(phthalic anhydride) (I¹) and a reaction is performed in the presence of an appropriate organic solvent.

In the above formula, $Z^1$ represents a single bond or a bivalent organic group. As the bivalent organic group, there can be illustrated, for example, the following groups. That is, there can be given bivalent atomic groups such as O, S, SO and $SO_2$; the following aryl groups:

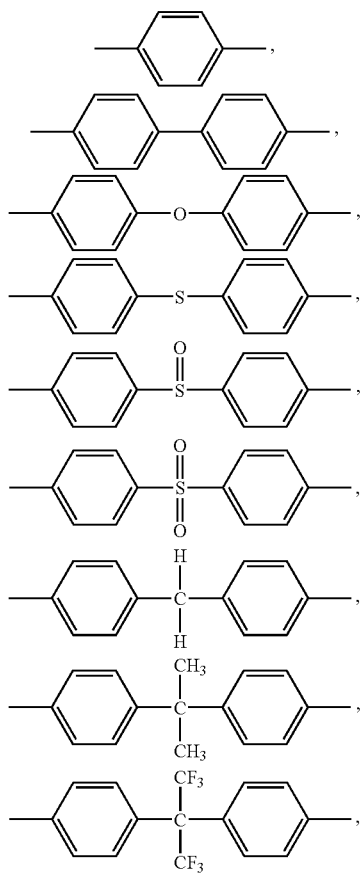

[wherein, the above-mentioned aryl groups may be substituted with (a) group(s) selected from the group consisting of a halogen atom, a methyl group and trifluoromethyl group.];

the following aryloxy groups

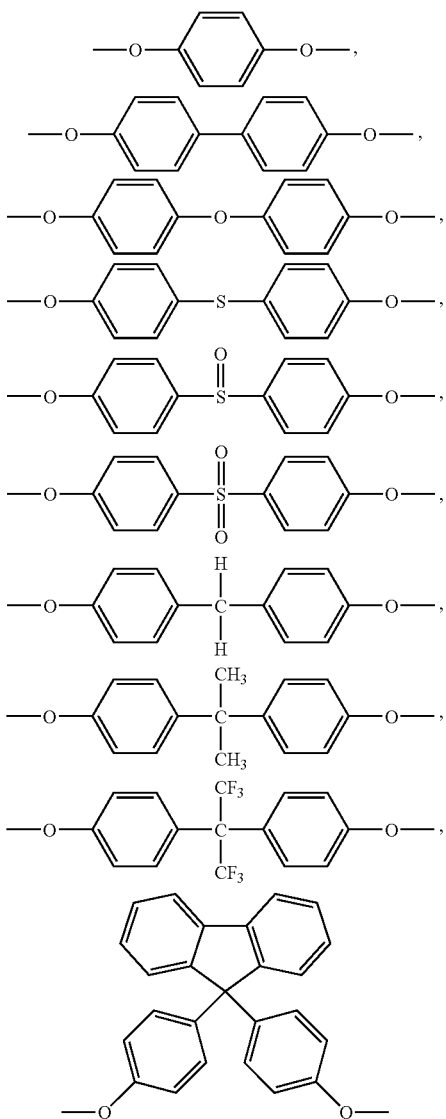

[wherein, the above-mentioned aryloxy groups may be substituted with (a) group(s) selected from the group consisting of a halogen atom, a methyl group and trifluoromethyl group]; and the following arylthio groups:

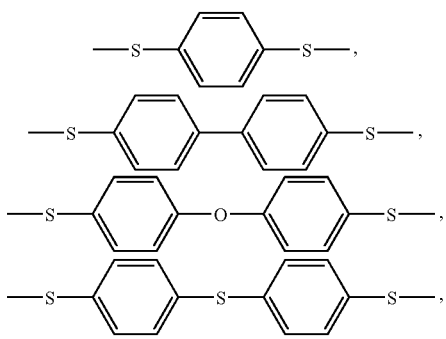

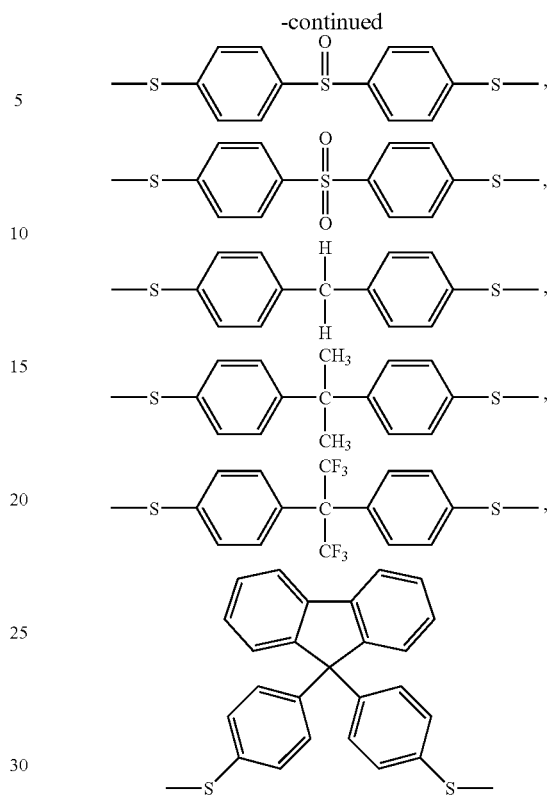

[wherein, the above-mentioned arylthio groups may be substituted with (a) group(s) selected from the group consisting of a halogen atom, a methyl group and trifluoromethyl group.].

As the $Z^1$ group, a bivalent organic group is preferred and a particularly preferred group is the following group:

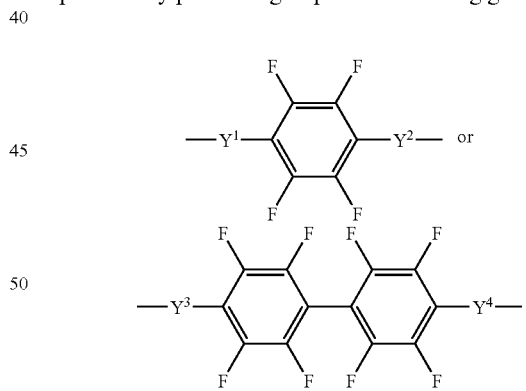

[wherein, $Y^1$ to $Y^4$ are independently represent oxygen atom or sulfur atom, but these all preferably are oxygen atoms].

As a halogen atom, a fluorine atom and/or a fluorine atom is preferred, and a fluorine atom is more preferred.

In a definition of compounds of the present invention, m and n may be different from one another, but these are preferably the same.

The "aliphatic carboxylic anhydride" used in the present invention is a substance which can capture water molecules produced by dehydration of the fluorinated bis(phthalic acid) compound ($II^1$) and is not particularly limited as long as it does not inhibit a reaction according to the present invention. For example, acetic anhydride, propionic anhydride, succinic anhydride and maleic anhydride can be mentioned and the acetic anhydride can be preferably used.

As the "organic solvent" of the present invention, there is used a solvent which has the moderate ability to dissolve toward the fluorinated bis(phthalic acid) compound ($II^1$), which is a raw material compound, and can moderately suppresses the excessive dehydration reaction due to use of an aliphatic carboxylic anhydride. Accordingly, the "organic solvent" used in the present invention does not include the aliphatic carboxylic anhydride. As such a "organic solvent", there can be given, for example, as aromatic hydrocarbons: benzene; substituted benzene derivatives such as toluene, xylene, mesitylene, ethylbenzene, propylbenzene, cumene, butylbenzene, tetralin, or the like; as aliphatic hydrocarbons having 6 or more carbon atoms: linear aliphatic hydrocarbons such as hexane, heptane, octane, nonane, decane, dodecane, or the like; alicyclic hydrocarbons such as cyclohexane and decalin; as dialkyl ether of which at least one alkyl group has 3 or more carbon atoms: propyl ether, butyl ether, or the like; and as ketones: methyl ethyl ketone and acetophenone. Among them, aromatic hydrocarbons and/or aliphatic hydrocarbons are preferably used, more preferably aromatic hydrocarbons.

With respect to a reaction, the "organic solvent", the "fluorinated bis(phthalic acid) compound ($II^1$)", which is a raw material compound, and the "aliphatic carboxylic anhydride" are mixed, and a reaction temperature is increased gradually to such an extent that a dehydration reaction does not proceed in excess and on the contrary a reaction efficiency does not become a problem.

The concentration of the fluorinated bis(phthalic acid) compound ($II^1$) with respect to the organic solvent at the initiation of reaction is preferably 0.05 to 0.7 g/ml, more preferably 0.07 to 0.4 g/ml. The reason for this is that when the concentration is less than 0.05 g/ml, the reaction efficiency may be poor, and when it is more than 0.7 g/ml, a dehydration reaction between molecules may become prone to occur.

An amount of an aliphatic carboxylic anhydride to be added is preferably 3 to 20 molar equivalent with respect to the fluorinated bis(phthalic acid) compound ($II^1$), more preferably 5 to 15 molar equivalent. The reason for this is that when this amount is less than 3 molar equivalent, the reaction efficiency may still be poor, and when it is more than 20 molar equivalent, the reaction may proceed in excess and the recovery of an intended compound becomes difficult because of high solubility of the intended compound in the aliphatic carboxylic anhydride.

A proper reaction temperature is not particularly limited because it varies depending on organic solvents and raw material compounds to be used, but a temperature of 50 to 200° C. is usually employed. A reaction time is not also particularly limited because it varies depending on organic solvents and reaction temperatures to be used, but a reaction time of 1 to 10 hours is generally employed.

After the completion of the reaction, it is preferred to crystallize a fluorinated bis(phthalic anhydride) ($I^1$), which is an intended compound, by adding a poor solvent to a reaction solution after cooling the reaction solution to about 10 to 70° C. The reason for this is that when water is used in aftertreatment, the cleavage of a anhydride structure may occur and the fluorinated bis(phthalic anhydride) ($I^1$) crystallized by adding a poor solvent after reacting under the above-mentioned reaction conditions has a large specific surface area and excellent solubility, and has the high usefulness as a raw material compound for the following steps.

The "poor solvent" to be used in this step is not particularly limited as long as it is one which can crystallize the fluorinated bis(phthalic anhydride) ($I^1$), which is an intended compound, and may be selected depending on properties of the intended-compound, and aliphatic hydrocarbons such as hexane, heptane, octane, nonane, decane, dodecane, or the like can be used as the poor solvent.

The obtained crystal may be dried after filtration. Further, it may be washed with a solvent, having low solubility for the fluorinated Bis(phthalic anhydride) ($I^1$) and a low boiling point, before drying.

The fluorinated bis(phthalic anhydride) ($I^1$) of the present invention obtained by the above-mentioned method has the following characteristics. That is, its specific surface area is 3.0 $m^2$/g or larger. The anhydride having a larger specific surface area dissolves in a solvent more easily and this can makes the next process more efficient particularly in a plant level of mass synthesis. Therefore, the specific surface area is more preferably 3.5 $m^2$/g or larger and furthermore preferably 4.0 $m^2$/g or larger. The specific surface area can be measured using a general Brunauer-Emmerit-Teller (BET) method.

Molar absorption coefficient of the fluorinated bis(phthalic anhydride) ($I^1$) of the present invention is 0.6 L/mol·cm or less at a wavelength of 360 nm. The reason for this is that when the molar absorption coefficient is more than 0.6 L/mol·cm, polyimide of a final product may color and produce an adverse effect particularly if such a polyimide used as optical materials. Therefore, the molar absorption coefficient is preferably 0.5 L/mol·cm or less, more preferably 0.4 L/mol·cm or less.

Among the fluorinated bis(phthalic acid) compound ($II^1$) which is a raw material compound for producing the fluorinated bis(phthalic anhydride) ($I^1$) of the present invention, the fluorinated bis(phthalic acid) compound ($II^2$), in which a $Z^1$ group is a bivalent organic group, can be produce by the following scheme:

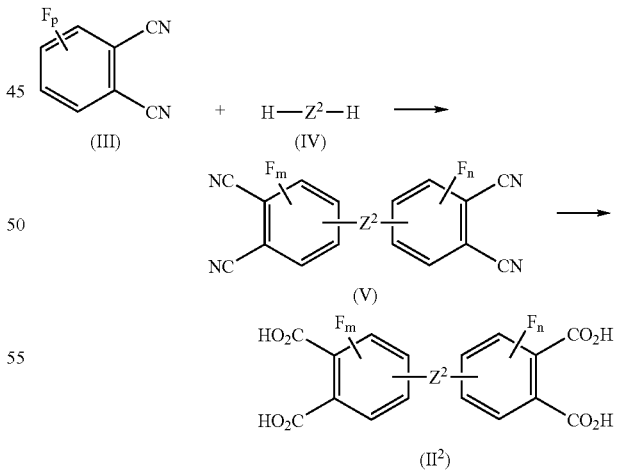

[wherein, p represents an integer of 2 to 4, $Z^2$ represents a bivalent organic group as defined for $Z^1$, and m and n independently represent integers of 1 to 3.]

In the above formulae, m and n may be different from one another, and in that case, two kinds of compounds (III) in which values of p are different from each other may be used as raw materials. However, in that case, it becomes difficult to purify the fluorinated bis(phthalonitrile) compound (V), so that it is preferred to synthesize a compound (V) in which values of m and n are the same by using a single compound (III). Specifically, as $Z^2$, there can be given a substance similar to the specific example of the bivalent organic group among $Z^1$ described above.

At the first stage of the above-mentioned scheme, a side reaction, in which the compound formed by condensing the compound (III) and the compound (IV) in proportions of 1:1 is condensed not with the compound (III) but with the compound (V) produced, may occur. Therefore, in order to suppress such the side reaction, it is necessary to use the compound (III) in excess. In doing so, an amount of the compound (III) to be used is preferably 8 to 50 molar equivalent with respect to the compound (IV) (more preferably 15 to 30 molar equivalent). When the compound (III) is used too much excessively, the demerit of a complicated purification process exceeds an effect of suppressing the side reaction (refer to Japanese Unexamined Patent Publications No. 6-16615).

Preferably, a reaction at the first stage of the above-mentioned scheme is performed by adding dropwise a solution of the compound (IV) to a solution of the compound (III). The reason for this is that the side reaction can be suppressed more efficiently by allowing the reaction to proceed in a condition where the compound (III) always presents in excess.

The solvent used in this scheme is not particularly limited as long as it can dissolve the raw material compounds therein and does not inhibit the reaction, and as examples of the solvent, ketones such as methyl isopropyl ketone, methyl isobutyl ketone, or the like; fatty acid esters such as ethyl acetate, isopropyl acetate, or the like; and nitrites such as benzonitrile, or the like can be given.

Further, it is preferred to add a basic compound to a reaction system to promote a reaction. As examples of such the basic compound, there can be given fluorides of alkali metal such as sodium fluoride, potassium fluoride and the like; fluorides of alkaline-earth metal such as calcium fluoride, magnesium fluoride and the like; and tertiary amines such as trimethylamine, triethylamine and the like.

A reaction temperature in adding dropwise the solution of the compound (IV) is not particularly limited, but it is preferred to heat in order to promote the reaction and a suitable reaction temperature is 40 to 100° C. When this temperature increases too much high due to the proceeding of the reaction, this temperature may be restricted to some degree during adding dropwise and it may be raised after adding dropwise. It is also important to adjust the reaction temperature so as not to substantially exceed a boiling point of a solvent to be used.

A reaction time varies depending on the kinds of raw materials, solvents and reaction temperatures to be used, but it is generally 1 to 24 hours, and specifically aftertreatment may be started after recognizing the completion of the reaction with thin-layer chromatography or the like.

After the completion of the reaction, a reaction solution is cooled at least to room temperature, and when a basic compound is precipitated, it is removed by filtration or the like. Further, the reaction solution is preferably washed with an aqueous solvent several times in order to remove the basic compound.

After removing the basic compound from the reaction solution, the solvent is distilled off. A residue is mainly composed of the compound (III), which is a raw material, and the intended compound (V).

In the present invention, by adding the organic solvent to such the residue, the fluorinated bis(phthalonitrile) compound (V), which is an intended compound, is preferentially obtained. That is, the "organic solvent" used in the present invention refers to a substance which has the excellent ability to dissolve toward the compound (III) and on the contrary the low ability to dissolve toward the compound (V) (preferably, substantially not dissolving the compound (V) at room temperature). Suitably, aromatic hydrocarbons, for example, non-substituted aromatic hydrocarbons such as benzene; and substituted aromatic hydrocarbons having substituent(s) toluene, xylene, or the like and/or aliphatic hydrocarbons, for example, linear aliphatic hydrocarbons such as hexane, octane, or the like; and alicyclic hydrocarbons such as cyclohexane, or the like are used The intended compound precipitated may be further subjected to a general purification process such as recrystallization after being separated by filtration or the like.

Additionally, it is also possible to substantially dissolve the intended compound (V) by increasing once the temperature of a mixture to a reflux temperature after adding the organic solvent to the above-mentioned residue and thereafter to recrystallize the intended compound (V) by cooling slowly the mixture to room temperature. According to this method, the intended compound (V) having a higher purity can be easily obtained.

The resulting fluorinated bis(phthalonitrile) compound (V) is then hydrolyzed to form the fluorinated bis(phthalic acid) compound ($II^2$). Such the hydrolysis reaction is conducted under a acidic condition, because a fluorine atom group may be attacked under basic conditions. The detailed reaction conditions are not particularly limited, but for example, by using an organic acid, which is liquid at room temperature, such as formic acid, acetic acid and propionic acid as a solvent, inorganic acid such as sulfuric acid, hydrochloric acid and phosphoric acid is added to the compound (V), and the mixture is reacted at 20 to 300° C. for 0.1 to 40 hours. Then, the resulting fluorinated bis(phthalic acid) compound ($II^2$) may be converted to the fluorinated bis(phthalic anhydride) by the dehydration reaction described above.

The fluorinated bis(phthalic anhydride) ($I^1$) of the present invention can be converted to a polyamic acid (VII) by the following scheme:

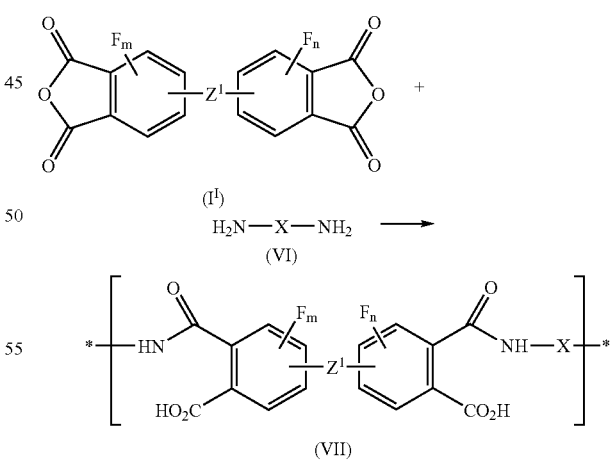

[wherein, m, n and $Z^1$ represent the same one as described above, and X represents a bivalent organic group.]

Specifically, as X (bivalent organic group) in the above-mentioned formula, there can be given a group similar to the specific example of $Z^1$ described above. As preferable X, there can be presented, for example, a substance represented by the following formula (X¹), and as more preferable X, there can be presented a substance represented by the following formula (X²):

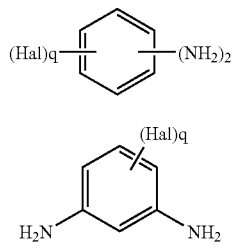

[in the above-mentioned formula, "Hal" represents a halogen atom (preferably a fluorine atom and/or a fluorine atom, or a fluorine atom), and q represents an integer of 1 to 3.]

Specifically, as X, there can be given the following compounds without being limited to the above-mentioned formulae: 2,4-diaminotoluene, 2,4-diaminoxylene, 2,4-diaminodurene, 4-(1H,1H,11H-eicosafluoroundecanoxy)-1,3-diaminobenzene, 4-(1H,1H-perfluoro-1-butanoxy)-1,3-diaminobenzene, 4-(1H,1H-perfluoro-1-heptanoxy)-1,3-diaminobenzene, 4-(1H,1H-perfluoro-1-octanoxy)-1,3-diaminobenzene, 4-pentafluorophenoxy-1,3-diaminobenzene, 4-(2,3,5,6-tetrafluorophenoxy)-1,3-diaminobenzene, 4-(4-fluorophenoxy)-1,3-diaminobenzene, 4-(1H,1H,2H,2H-perfluoro-1-hexanoxy)-1,3-diaminobenzene, 4-(1H,1H,2H,2H-perfluoro-1-dodecanoxy)-1,3-diaminobenzene, p-phenylenediamine, 2,5-diaminotoluene, 2,3,5,6-tetramethyl-p-phenylenediamine, 2,5-diaminobenzotrifluoride, bis(trifluoromethyl)phenylenediamine, diamino-tetra(trifluoromethyl)benzene, diamino(pentafluoroethyl)-benzen, 2,5-diamino(perfluorohexyl)benzene, 2,5-diamino(perfluorobutyl)benzene, Benzidine, 2,2'-dimethylbenzidine, 3,3'-dimethylbenzidine, 3,3'-dimethoxylbenzidine, 2,2'-dimethoxylbenzidine, 3,3'-tetramethylbenzidine, 5,5'-tetramethylbenzidine, 3,3'-diacetylbenzidine, 2,2'-bis(trifluoromethyl)-4,4'-diaminobiphenyl, octafluorobenzidine, 3,3'-bis(trifluoromethyl)-4,4'-diaminobiphenyl, 4,4'-diaminodiphenylether, 4,4'-diaminodiphenylmethane, 4,4'-diaminodiphenylsulfone, 2,2-bis(p-aminophenyl)propane, 3,3'-dimethyl-4,4'-diaminodiphenylether, 3,3'-dimethyl-4,4'-diaminodiphenylmethane, 1,2-bis(anilino)ethane, 2,2-bis(p-aminophenyl)hexafluoropropane, 1,3-bis(anilino)-hexafluoropropane, 1,4-bis(anilino)octafluorobutane, 1,5-bis(anilino) decafluoropentane, 1,7-bis(anilino)-tetrafluoroheptane, 2,2-bis(trifluoromethyl)-4,4'-diaminodiphenylether, 3,3'-bis(trifluoromethyl)-4,4'-diaminodiphenylether, 3,3',5,5'-tetrakis(trifluoromethyl)-4,4'-diaminodiphenylether, 3,3'-bis(trifluoromethyl)-4,4'-diaminobenzophenone, 4,4'''-diamino-p-terphenyl, 1,4-bis(p-aminophenyl)benzene, p-bis(4-amino-2-trifluoromethylphenoxy)benzene, bis(aminophenoxy)-bis(trifluoromethyl)benzene, bis(aminophenoxy)-tetrakis(trifluoromethyl)benzene, 4,4'''-diamino-pquaterphenyl, 4,4'-bis(p-aminophenoxy)biphenyl, 2,2-bis[4-(p-aminophenoxy)phenyl]propane, 4,4'-bis(3-aminophenoxy-phenyl)diphenylsulfone, 2,2-bis[4-(4-aminophenoxy)phenyl]-hexafluoropropane, 2,2-bis[4-(3-aminophenoxy)phenyl]-hexafluoropropane, 2,2-bis[4-(2-aminophenoxy)phenyl]-hexafluoropropane, 2,2-bis[4-(4-aminophenoxy)-3,5-dimethylphenyl]hexafluoropropane, 2,2-bis[4-(4-aminophenoxy)-3,5-ditrifluoromethylphenyl] hexafluoropropane, 4,4'-bis(4-amino-2-trifluoromethylphenoxy)biphenyl, 4,4'-bis(4-amino-3-trifluoromethylphenoxy)biphenyl, 4,4'-bis(4-amino-2-trifluoromethylphenoxy)diphenylsulfone, 4,4'-bis(3-amino-5-trifluoromethylphenoxy)diphenylsulfone, 2,2-bis[4-(4-amino-3-trifluoromethylphenoxy)phenyl] hexafluoropropane, bis[(trifluoromethyl)aminophenoxy] biphenyl, bis{[(trifluoromethyl)aminophenoxy]phenyl}hexafluoropropane, diaminoanthraquinone, 1,5-diaminonaphthalene, 2,6-diaminonaphthalene, bis{2-[(aminophenoxy)phenyl]-hexafluoroisopropyl}benzene, bis (2,3,5,6-tetrafluoro-4-aminophenyl)ether, bis(2,3,5,6-tetrafluoro-4-aminophenyl)-sulfide, 1,3-bis(3-aminopropyl) tetramethyldisiloxane, 1,4-bis(3-aminopropyldimethylsilyl) benzene, bis(4-aminophenyl)diethylsilane, 1,4-diaminotetrafluorobenzene, 4,4'-bis (tetrafluoroaminophenoxy)-octafluorobiphenyl.

As the reaction conditions in the above scheme, common conditions may be employed. For example, a fluorinated bis (phthalic anhydride) (I¹) and a diamine compound (VI) may be dissolved in a solvent, and reacted at 20 to 50° C., preferably at room temperature, for 2 to 7 days (refer to Japanese Unexamined Patent Publications No. 6-1914). The solvent used in this scheme is not particularly restricted as long as it can moderately dissolve the compounds (I¹) and (VI) and does not inhibit the reaction, and for example, amides such as dimethylformamide, dimethylacetamide, or the like and N-methylpyrrolidone can be used. After the completion of the reaction, it may be purified, and it may also be used as a component for varnish or varnish itself, as it is.

When a solution containing the polyamic acid (VII) of the present invention is used as varnish, it may be applied, as it is, to a base by spin coating and the like. The base used in this case is not particularly limited and for example, plastic materials such as polyimide resin, polyamide resin and the like; quartz glass; and multicomponent glass can be used for producing optical materials, and silicon can be used for wiring board products.

After varnish is coated to the base, it is dried by heating depending on an amount of varnish applied, generally at a temperature of 50 to 500° C. for 1 to 12 hours to obtain polyimide represented by the following formula (VI):

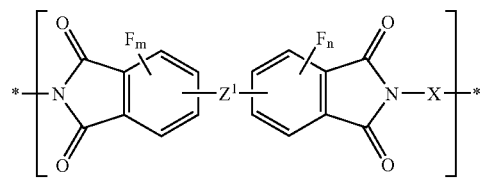

[wherein, m, n, Z¹ and X represent the same one as described above.] This drying is preferably conducted in an atmosphere of inert gases such as nitrogen gas, argon gas, or the like, and a drying temperature is preferably elevated gradually in order to prevent uneven drying or the like.

The polyimide (VIII) of the present invention thus obtained is polyimide of high quality, the coloration of which is reduced, and is extremely useful as optical materials.

Hereinafter, the present invention will be described in more detail by way of examples, but these examples do not limit the present invention.

EXAMPLES

Preparation Example 1

Preparation of 1,4-bis(3,4-dicyano-2,5,6-trifluorophenoxy)tetrafluorobenzene

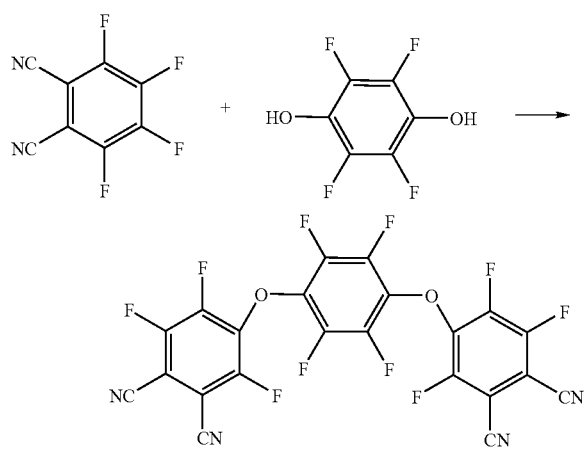

Into a 200 milliliter—four necked flask equipped with a stirrer, a cooling reflux tube, a thermometer and a dropping apparatus, 60.52 g (0.30 mol) of 3,4,5,6-tetrafluorophthalonitrile, 5.50 g (0.095 mol) of potassium fluoride and 100 g of methyl isobutyl ketone were added, and the mixture was heated to 50° C. A solution formed by dissolving 5.50 g (0.030 mol) of tetrafluorohydroquinone in 9 g of methyl isobutyl ketone was added dropwise from the dropping apparatus over 15 minutes. Then, the mixture was reacted at 50° C. for 2 hours and subsequently at 80° C. for 3 hours.

After the completion of the reaction, a reaction solution was cooled to room temperature and filtered out to separate potassium fluoride, and the like. The obtained filtrate was washed three times with 40 g of 5% aqueous sodium sulfate solution, and then methyl isobutyl ketone was distilled off. After 50 g of toluene was added to the residue and this mixture was heated to a reflux temperature, it was cooled to room temperature. A precipitated substance was filtered out and a filtered precipitate was washed with 25 g of toluene. By drying this filtered precipitate, 15.77 g (0.029 mol) of the title compound was obtained (yield with respect to tetrafluorohydroquinone: 97%). A purity of the resulting title compound was measured by liquid chromatography to give 95%.

In addition, 45 g of 3,4,5,6-tetrafluorophthalonitrile which is a raw material compound remained in the filtrate. By distilling off toluene from the filtrate and further distilling at a distillation temperature of 110° C. under vacuum of 1.3 kPa, 25 g of 3,4,5,6-tetrafluorophthalonitrile was recovered. In doing so, since a fluorinated phthalonitrile derivative, which is an intended compound, remained few, a problem of solidification did not occurred.

Preparation Example 2

Preparation of 1,4-bis(3,4-dicyano-2,5,6-trifluorophenoxy)tetrafluorobenzene 15.68 g (0.029 mol) of the title compound was obtained in the same manner as that of Preparation Example 1 (yield with respect to tetrafluorohydroquinone: 96%). 66 g of toluene and 46 g of 3,4,5,6-tetrafluorophthalonitrile were contained in the filtrate after filtering the title compound.

This filtrate was added to a residue obtained by distillation in the above-mentioned Preparation Example 1. By distilling off toluene from the mixture and further distilling at a distillation temperature of 110° C. under vacuum of 1.3 kPa, 45 g of 3,4,5,6-tetrafluorophthalonitrile was recovered. 21 g of 3,4,5,6-tetrafluorophthalonitrile was contained in a residue by distillation.

Comparative Preparation Example 1

Preparation of 1,4-bis(3,4-dicyano-2,5,6-trifluorophenoxy)tetrafluorobenzene 60.52 g (0.30 mol) of 3,4,5,6-tetrafluorophthalonitrile and 5.50 g (0.030 mol) of tetrafluorohydroquinone were used as starting materials, and a reaction was performed under the same conditions as that of the above-mentioned Preparation Example 1.

After the completion of the reaction, a reaction solution was cooled to room temperature, and filtered out to separate potassium fluoride, and the like. The obtained filtrate was washed three times with 40 g of 5% aqueous sodium sulfate solution, and then methyl isobutyl ketone was distilled off. Further, 3,4,5,6-tetrafluorophthalonitrile, which was a starting and was still present excessively, was distilled at a distillation temperature of 110° C. under vacuum of 1.3 kPa. By this distillation, 44 g of 3,4,5,6-tetrafluorophthalonitrile could be recovered, but a residue on distillation was solidified at a time when distillate was not present. A melting point of this residue by distillation was 160° C. or higher.

20 g of toluene was added to the residue after being distilled off, and after this mixture was heated to a reflux temperature, it was cooled to room temperature. A precipitated substance was filtered and a filtered precipitate was washed with 20 g of toluene. By drying this filtered precipitate, 15.61 g (0.029 mol) of the title compound was obtained (yield with respect to tetrafluorohydroquinone: 96%). A purity of the resulting title compound was measured by liquid chromatography to give 94%.

Consideration

As shown in the above Preparation Examples 1 and 2, according to the present invention, it becomes possible to purify the fluorinated phthalonitrile compound without distilling the raw material compound and the yield and the purity of the intended compound obtained are equivalent to the case of purification by distillation.

Further, since few fluorinated phthalonitrile compound, which is an intended compound, is contained in the filtrate after separating the intended compound in a purification process, it is not necessary to consider the instability of the intended compound toward heat in a process of recovering the raw material compound by distillation. Furthermore, since a problem that the intended compound solidifies as the raw material compound is distilled off does not a rise, it was verified that it is possible to efficiently recover the raw material compound by distillation without restriction.

Preparation Example 3

Preparation of 1,4-bis(3,4-dicarboxy-2,5,6-trifluorophenoxy)tetrafluorobenzene

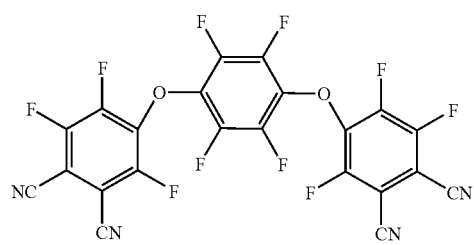

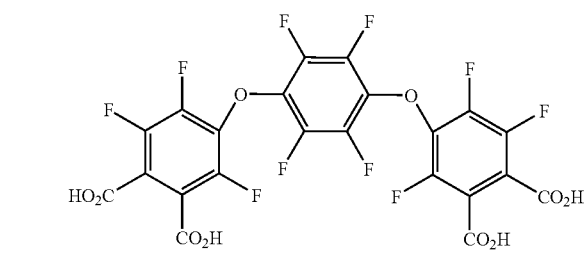

Into a one liter—four necked flask were charged 50 g of 1,4-bis(3,4-dicyano-2,5,6-trifluorophenoxy)tetrafluorobenzene obtained in the above-mentioned Preparation Examples 1 and 2 and 350 ml of propionic acid. To this mixture, 150 ml of 70% by mass sulfuric acid was added dropwise over 1 hour while stirring at 120° C. After adding dropwise, the mixture was refluxed for 6 hours and then cooled, and poured into 1.5 liters of ice water. The resulting intended compound had a purity of 95.7%.

Next, the deposited crude intended compound was filtered and recrystallized with 400 ml of 10% by mass aqueous acetone solution. This crystal had a purity of 98.7%. By repeating a similar recrystallization step once more and drying the obtained crystal at 100° C. for 5 hours, 43.0 g of the intended compound was obtained (yield: 75%). The finally obtained intended compound had a purity of 99.7%. The purity of the intended compound was measured by liquid chromatography under the following condition.

Conditions of Liquid Chromatography
  Column: Intersil ODS 2 (manufactured by GL Sciences Inc.), particle size: 5 m, 46×250 mm
  Eluent: acetonitrile/(5 mM tetrabutylammonium chloride+5 mM aqueous ammonium dihydrogenphosphate solution)=50/50
  Detector: UV 285 nm

Preparation Example 4

Preparation of 4,4'-[(2,3,5,6-tetrafluoro-1,4-phenylene)bis(oxy)]bis(3,5,6-trifluorophthalic anhydride)

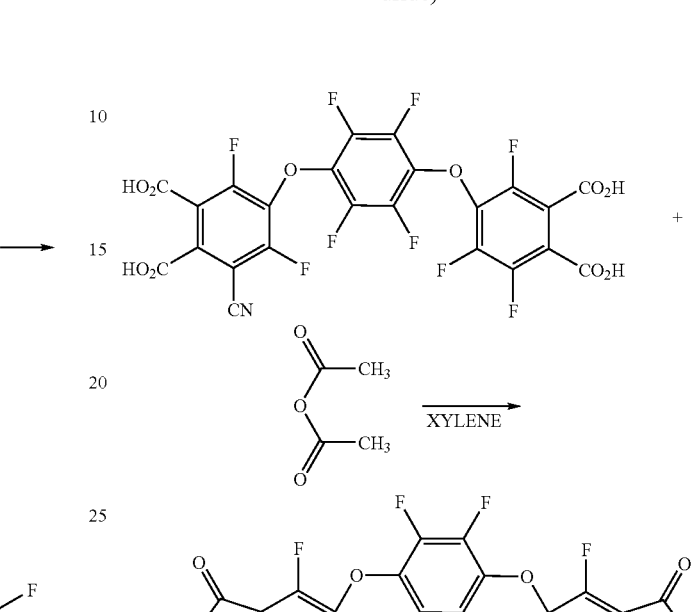

Into a three liter—four necked flask were charged 135 g (0.218 mol) of 1,4-bis(3,4-dicarboxy-2,5,6-trifluorophenoxy)-tetrafluorobenzene obtained in Preparation Example 3, 1290 ml of xylene and 220 ml (2.332 mol) of acetic anhydride. This mixture was gradually heated and changed to a homogeneous solution, and then stirred at 130° C. for about 2 hours.

Then, the reaction solution was cooled to 65° C. and it crystallized out into crystals by adding 1350 ml of n-hexane. After being further cooled, the resulting crystal was filtered and washed twice with 200 ml of n-hexane. By drying this crystal under vacuum, 125 g (0.124 moles, yield: 98%) of the title compound was obtained.

Comparative Preparation Example 2

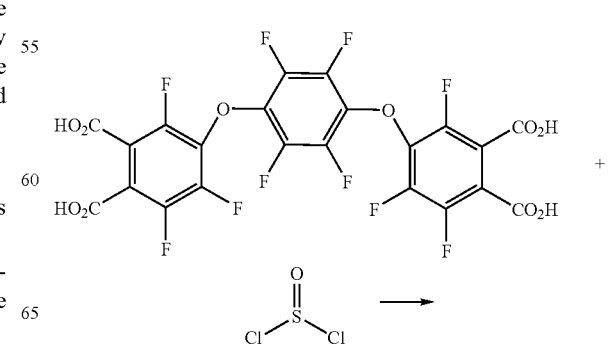

-continued

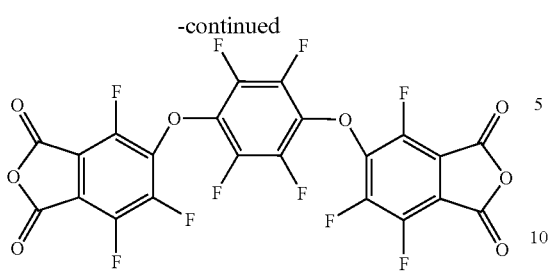

Into a three liter—four necked flask were charged 135 g (0.218 mol) of 1,4-bis(3,4-dicarboxy-2,5,6-trifluorophenoxy)-tetrafluorobenzene and 1.12 kg (9.41 mol) of thionyl chloride. The temperature of this mixture was increased to 75° C. over 1 hour and the mixture was reacted under reflux for 25 hours.

After recognizing that a peak of a carboxylic acid disappeared in infrared spectrum analysis of the reacted solution, most of thionyl chloride was distilled off from the reacted solution and 300 ml of toluene was added. After being cooled, the obtained crystal was filtered and washed twice with 50 ml of toluene. By drying this crystal under vacuum, 124 g (0.212 mol, yield: 97%) of the title compound was obtained.

Test Example 1

Each specific surface area of 4,4'-[(2,3,5,6-tetrafluoro-1,4-phenylene)bis(oxy)]bis(3,5,6-trifluorophthalic anhydride) obtained in the above-mentioned Preparation Example 4 and Comparative Preparation Example 2 was measured.

The specific surface area was measured using a Brunauer-Emmerit-Teller (BET) method (Model NOVA 2000 manufactured by Quantachrome Corporation). The results of measurements are shown in Table 1.

TABLE 1

|  | Preparation Example 4 | Comparative Preparation Example 2 |
|---|---|---|
| Specific surface area ($m^2$/g) | 4.403 | 2.869 |

As shown in these results, the fluorinated bis(phthalic anhydride) of the present invention had a larger specific surface area than the conventional compound, and therefore it was verified that this can be quickly dissolved in a solvent and can enhance the efficiency of the next step in a plant level of mass synthesis.

Test Example 2

0.5 g of 4,4'-[(2,3,5,6-tetrafluoro-1,4-phenylene)-bis(oxy)]bis(3,5,6-trifluorophthalic anhydride) obtained in the above-mentioned Preparation Example 4 was dissolved in acetone and adjusted so as to give 10 g of the total amount of the mixture. The absorbance in the visible region of this solution was measured with a spectrophotometer (UV-3100 manufactured by Shimadzu Corporation). The absorbance of the same compound prepared in the above-mentioned Comparative Preparation Example 2 was similarly measured. The results of measurement were shown in Table 2.

TABLE 2

|  | Wavelength | Preparation Example 4 | Comparative Preparation Example 2 |
|---|---|---|---|
| Molar absorption coefficient (L/mol · cm) | 360 nm | 0.258 | 0.672 |

As shown in these results, the fluorinated bis(phthalic anhydride) of the present invention had a reduced coloration compared with the conventional compound. Therefore, it was demonstrated that the fluorinated bis(phthalic anhydride) of the present invention was particularly useful as a synthetic intermediate of optical materials.

Preparation Example 5

Preparation of Polyamic Acid According to the Present Invention

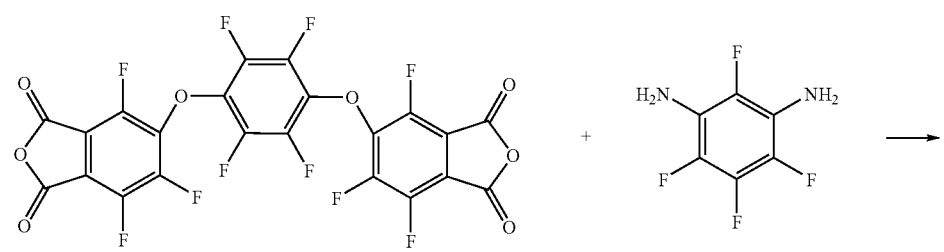

-continued

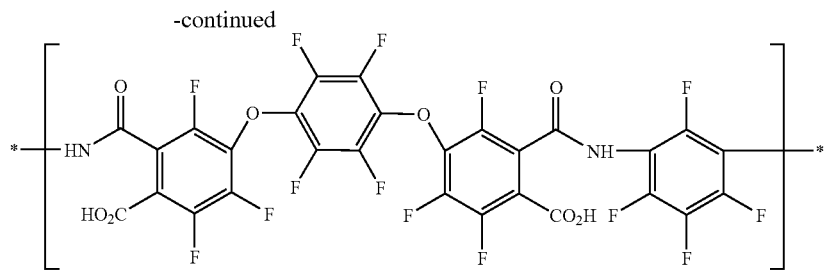

Into a 100 milliliter—three necked flask were charged 14.51 g (24.92 mmol) of 4,4'-[(2,3,5,6-tetrafluoro-1,4-phenylene)bis(oxy)]bis(3,5,6-trifluorophthalic anhydride) obtained in Preparation Example 4, 4.48 g (24.92 mmol) of 1,3-diamino-2,4,5,6-tetrafluorobenzene and 31 g of N,N-dimethylacetamide. As this mixture was stirred at room temperature in an atmosphere of nitrogen, it took about 30 minutes before it became a homogeneous solution. By leaving standing further for 4 days, a light-yellow polyamic acid solution having a high viscosity was obtained.

Next, when a molecular weight of the resulting polyamic acid was measured by gel permeation chromatography (GPC), its weight-average molecular weight was $1.01 \times 10^5$. The condition of the GPC was as follows.

Column: TSK gel α-M×2 (manufactured by TOSOH CORP.)
Eluent: 10 mM LiBr+10 mM $H_3PO_4$ dimethylacetamide solution
Flow rate: 1.0 ml/min
Apparatus: HLC-8220GPC (manufactured by TOSOH CORP.)
Detection: UV 270 nm Comparative Preparation Example 3

Preparation of Polyamic Acid

Raw materials were charged into a three necked flask in the same manner as that of the above-mentioned Preparation Example 5 except for using a substance obtained in the above Comparative Preparation Example 2 instead of a substance obtained in the above Preparation Example 4 as the 4,4'-[(2,3,5,6-tetrafluoro-1,4-phenylene)bis(oxy)]bis(3,5,6-trifluorophthalic anhydride). As this mixture was stirred at room temperature as with the above-mentioned Preparation Example 5, it took about 1 hour before it became a homogeneous solution. By leaving standing further for 4 days, a yellow polyamic acid solution was obtained, but its viscosity was low. When its weight-average molecular weight was measured in the same manner as that of the above-mentioned Preparation Example 5, it was $6.04 \times 10^4$.

Preparation Example 6

Preparation of Polyimide According to the Present Invention

The polyamic acid solution obtained in the above Preparation Example 5 was applied onto a silicon substrate 4 inches in diameter by spin coating and a polyimide film was formed on the silicon substrate by heating at 70° C. for 2 hours, at 160° C. for 1 hour, at 250° C. for 30 minutes and at 350° C. for 1 hour in an atmosphere of nitrogen.

Comparative Preparation Example 4

Preparation of Polyimide

A polyimide film was formed in the same manner as that of the above-mentioned Preparation Example 6 except for using polyamic acid solution obtained in the above-mentioned Comparative Preparation Example 3. However, the resulting film evidently exhibited more yellow coloration than the film obtained in the above Preparation Example 6.

Consideration

As shown in the above Preparation Example 5 and Comparative Preparation Example 3, though the conventional fluorinated bis(phthalic anhydride) had a relatively small specific surface area, that of the present invention had a larger specific surface area. Therefore, the fluorinated bis(phthalic anhydride) of the present invention could reduce a time to dissolve in a solvent.

Further, when a polyamic acid is produced by using the fluorinated bis(phthalic anhydride) of the present invention as a raw material, a polyamic acid, which has a larger molecular weight than that of the polyamic acid produced from the conventional fluorinated bis(phthalic anhydride) as a raw material, can be obtained, though the reason for this is not necessarily clarified. Accordingly, the molecular weight of the polyimide, a final product, also becomes large, and as a result of this, it becomes possible to produce polyimide having high mechanical strength.

Furthermore, since the coloration of the fluorinated bis(phthalic anhydride) of the present invention was reduced, the coloration of polyimide, which is a final product, could be suppressed.

INDUSTRIAL APPLICABILITY

Since the method for producing the fluorinated phthalonitrile compound according to the present invention does not need a process of removing the raw material compound, which has been excessively used, by distillation in purification process, it can be applied to a plant level of mass synthesis and is industrially very useful as one capable of producing efficiently.

Further, since the fluorinated bis(phthalic anhydride) of the present invention has a larger specific surface area, it has excellent solubility and therefore also suitable for a plant level of mass synthesis. Furthermore, since its coloration is reduced, the coloration of polyimide, which is a final product, is also similarly suppressed. Therefore, the fluorinated bis(phthalic anhydride) of the present invention is excellent as intermediate raw materials of optical materials, wiring board materials, photosensitive materials and liquid crystal materials and the like, so that the method for producing the same is also industrially extremely useful.

Although the present invention has been fully described by way of example, it is to be understood that various changes and modifications will be apparent to those skilled in the art. Therefore, unless otherwise such changes and modifications depart from the scope of the present invention hereinafter defined, they should be construed as being included therein. The scope of the present invention, therefore, should be determined by the following claims.

The patents, patent applications and publications cited herein are incorporated by reference.

What is claimed is:

1. A method for producing a fluorinated bis(phthalic anhydride) ($I^1$) from a fluorinated bis(phthalic acid) compound ($II^1$) as shown in the following formulae, comprising dehydrating fluorinated bis(phthalic acid) compound ($II^1$) using an aliphatic carboxylic anhydride in an organic solvent,

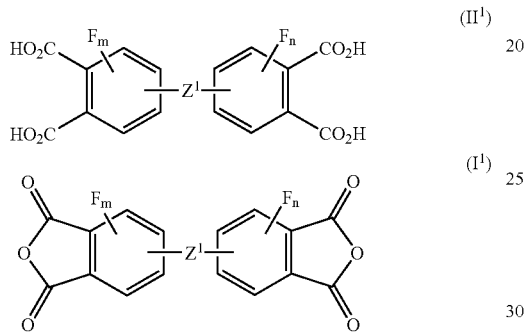

wherein m and n independently represent integers of 1 to 3, and $Z^1$ represents a single bond or a bivalent organic group selected from the group consisting of the following formulae:

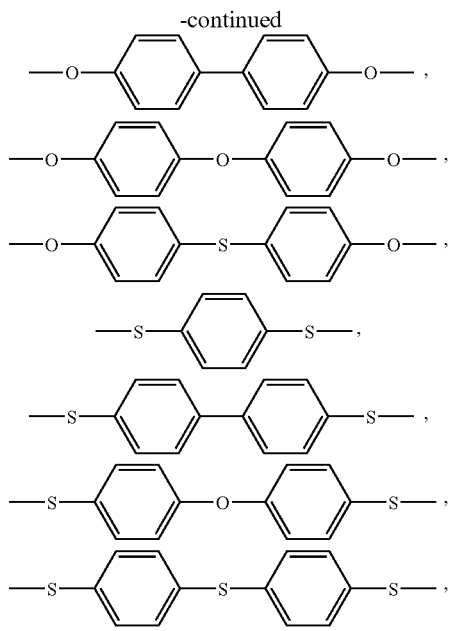

wherein the above aryloxy groups and arylthio groups may be substituted with one or more fluorine atoms.

2. The method of production according to claim 1, wherein the organic solvent is an aromatic hydrocarbon and/or an aliphatic hydrocarbon.

3. The method of production according to claim 1, wherein the fluorinated bis(phthalic anhydride) ($I^1$) is crystallized by adding a poor solvent after the completion of a reaction.

4. The method of production according to claim 2, wherein the fluorinated bis(phthalic anhydride) ($I^1$) is crystallized by adding a poor solvent after the completion of a reaction.

* * * * *